(12) United States Patent
Kao

(10) Patent No.: US 9,724,541 B2
(45) Date of Patent: Aug. 8, 2017

(54) DENTAL CLEANING AND POLISHING COMPOSITION COMPRISING DIAMOND PARTICLES

(75) Inventor: Lisa Marie Kao, Miami Beach, FL (US)

(73) Assignee: Lisa Marie Kao, Miami, FL (US)

( * ) Notice: Subject to any disclaimer, the term of this patent is extended or adjusted under 35 U.S.C. 154(b) by 0 days.

(21) Appl. No.: 12/418,927

(22) Filed: Apr. 6, 2009

(65) Prior Publication Data

US 2010/0254915 A1 Oct. 7, 2010

(51) Int. Cl.
- *A61K 6/00* (2006.01)
- *A61Q 11/00* (2006.01)
- *A61K 8/19* (2006.01)

(52) U.S. Cl.
CPC ............ *A61Q 11/00* (2013.01); *A61K 8/19* (2013.01); *A61K 2800/412* (2013.01)

(58) Field of Classification Search
USPC .......................................... 424/49, 401, 769
See application file for complete search history.

(56) References Cited

U.S. PATENT DOCUMENTS

| | | |
|---|---|---|
| 3,892,853 A | 7/1975 | Cobble |
| 4,021,263 A * | 5/1977 | Rosenblum ............... 106/474 |
| 4,482,538 A | 11/1984 | Davies |
| 4,528,180 A | 7/1985 | Schaeffer |
| 4,649,044 A * | 3/1987 | Gomi et al. ............... 424/49 |
| 4,702,905 A | 10/1987 | Mitchell et al. |
| 4,705,680 A | 11/1987 | Vellekoop |
| 4,814,160 A | 3/1989 | Carter et al. |
| 5,094,839 A * | 3/1992 | Lowder et al. ............ 424/49 |
| 5,275,561 A | 1/1994 | Goldsmith |
| 5,294,434 A | 3/1994 | King et al. |
| 5,700,449 A | 12/1997 | Katayama et al. |
| 5,776,435 A | 7/1998 | Gaffar et al. |
| 6,159,446 A | 12/2000 | Randive et al. |
| 6,162,418 A | 12/2000 | Randive et al. |
| 6,503,084 B2 | 1/2003 | Evers et al. |
| 7,979,946 B2 | 7/2011 | Kister et al. |
| 8,337,204 B2 | 12/2012 | Lowder et al. |
| 2005/0084551 A1* | 4/2005 | Jensen et al. ............ 424/769 |
| 2005/0220829 A1* | 10/2005 | Sung et al. .............. 424/401 |
| 2007/0140985 A1* | 6/2007 | Boyd et al. .............. 424/49 |
| 2009/0130031 A1* | 5/2009 | Herman .................... 424/49 |
| 2009/0130627 A1* | 5/2009 | Herman .............. A61K 8/19 433/142 |

\* cited by examiner

*Primary Examiner* — Walter Webb
(74) *Attorney, Agent, or Firm* — Steven Greenberg; CRGO Law

(57) ABSTRACT

A new whitening dentifrice suitable for use with porcelain veneers and dental work as well as with natural tooth enamel comprising diamond particles is disclosed.

22 Claims, No Drawings

DENTAL CLEANING AND POLISHING COMPOSITION COMPRISING DIAMOND PARTICLES

BACKGROUND OF THE INVENTION

Dentifrices are used to clean, bleach, whiten, and otherwise treat the teeth and gums. Generally, the active ingredients in a dentifrice are contained within a carrier.

For an abrasive, most toothpaste comprises various types of silica to debride and physically scrub the external surface of the teeth. This scrubbing action removes the organic film (i.e. the pellicle), formed of salivary proteins which covers the teeth and which is known to become stained and discolored by foods, such as coffee, tea and berries, as well as, by tobacco smoke, cationic antibacterials, and chromogenic bacteria. Such physical removal of the stained pellicle is a simple and effective means of removing the undesirable surface staining and discoloration which occurs daily. Further, such physical removal of the pellicle also removes plaque bacteria on the pellicle surface.

The carrier can be a paste (i.e., toothpaste) or a gel (i.e., brushing gels and bleaching gels) or an equivalent vehicle suitable for oral use. The dentifrice can be dispensed onto a brushing device or, in some cases, onto a tray, stint or mouth guard, and then the dental surfaces are brushed or polished for a sufficient period of time. "Gels" are thickened by a gelling agent that hydrogen bonds a dispersion medium to produce a semisolid, transparent, jelly-like material. In contrast, "pastes" are thickened by the addition of fillers. However, the line between gels and pastes is not always clear. Furthermore, sometimes dentifrices that are opaque and/or contain one or more abrasive fillers are labeled pastes, even if they exhibit gel-like properties. Therefore, in describing the present invention, the term "dentifrice" will be used to clearly indicate that both gels and pastes are embraced.

In dental polishing compositions, such as disclosed in prior U.S. Pat. Nos. 4,702,905; 4,528,180; 4,705,680 and 4,814,160, combinations of such ingredients are disclosed and are directed to dental creams, pastes and gels which incorporate the well-known cleaning or polishing components such as water-insoluble alkaline earth metal salts or similar agents.

These cleaning compositions are useful and satisfactory for manual brushing of teeth. However, these conventional agents are not satisfactory for use with cosmetic dental patients with porcelain veneers, caps or crowns. Harder and finer abrasives are typically necessary to accomplish a higher degree of polishing as opposed to mere cleaning of such surfaces to provide a smooth, mirror-like finish.

There exist presently, polishes that are used with cosmetic dental appliances which contain diamond particles, but they are designed for use in polishing porcelain and composite tooth restoration materials in "chairside applications" as well as being useful in laboratory and industrial applications. Products such as diamond particles in a glycerin base paste have been used in dental offices for years for porcelain crowns.

The use of diamond particulates in a dentifrice for use by patients at home has not previously been available due to the general understanding by those of ordinary skill in the dental or oral hygiene arts, that diamond particles are too abrasive for use on natural tooth enamel by the ordinary consumer.

BRIEF SUMMARY OF THE INVENTION

The dentifrice of the present invention can provide cleaning and a higher gloss than conventional compositions known in the art.

The instant invention is directed to a dentifrice (toothpaste, brushing gel, etc. . . . ). More specifically, the instant invention is directed to specifically cleaning cosmetic dental surfaces such as porcelain, composites and also natural teeth with a gel or paste comprising a diamond abrasive or diamond particulates such as diamond dust.

It has been surprisingly found that a dentifrice or polishing composition comprising diamond particulates can be prepared that will maintain the luster and gloss of porcelain dental work with low abrasion on natural tooth enamel. The composition may include many compounds useful in toothpastes and gels, such as flavoring agents, thickeners, stabilizing agents, colors, humectants and other compounds suitable for use in oral care applications.

In an embodiment, the invention provides a dentifrice or polishing composition comprising diamond particles. In another embodiment, the diamond particles are in an amount and size which is effective to maintain the luster and gloss of porcelain dental work with low abrasion on natural tooth enamel, such as diamond dust.

In an embodiment, the invention also provides a dentifrice or polishing composition comprising diamond particles which will also prevent dental caries by addition of sodium fluoride.

In another embodiment, the invention provides a dentifrice or polishing composition comprising diamond particles which also comprises other whitening or abrasive agents.

In yet another embodiment, the invention provides a dentifrice or polishing composition comprising diamond particles in a size and an amount effective to remove surface stains from porcelain dental appliances and tooth enamel.

In another embodiment the invention provides a method of cleaning or polishing a dental surface, wherein said method comprises the steps of applying the dentifrice or polishing composition of the present invention to a dental surface, and brushing said dental surface with said composition for a therapeutically effective period of time.

The invention, together with other features and advantages, which will become subsequently apparent, reside in the details of the technology as more fully hereinafter described and claimed.

DETAILED DESCRIPTION OF THE INVENTION

In describing embodiments of the invention, specific terminology will be resorted to for the sake of clarity. However, the invention is not intended to be limited to the specific terms so selected, and it is to be understood that each specific term includes all technical equivalents which operate in a similar manner to accomplish a similar purpose.

The following examples further illustrate the invention but, of course, should not be construed as in any way limiting its scope.

In the present invention, there is thus provided a dentifrice or polishing composition comprising diamond powder and at least one or more of the following components: xylitol, sodium fluoride, water, glycerin, sorbitol, silica, cocaimidopropyl betaine, and titanium dioxide.

In another embodiment, the above dentifrice or polishing composition may also comprise flavoring agents and sweetening agents.

The dentifrice or polishing composition of the present invention also may comprise binders such as xanthan gum and other gums, sodium alginate, sodium carboxymethylcellulose, carrageenan, xanthan gum, sodium polyacrylate, hydroxyethyl cellulose, hydroxypropyl cellulose, pectin, tragacanth gum, arabic gum, guar gum, karaya gum, locust bean gum, gellan gum, tamarind gum, Psyllium seed gum, polyvinyl alcohol, sodium chondroitin sulfate, and methoxyethylene-maleic anhydride copolymer. It is contemplated that binders can comprise between 0.1% and about 10% by weight of the composition.

In one embodiment it is contemplated that the dentifrice or polishing composition of the present invention comprises natural plant extracts, such as chamomile extract, and may also contain herbal extracts such as sage extract in a concentration range of about 0.1 to 5% by weight.

In an embodiment, the dentifrice or polishing composition comprises, in addition to the above-described components, a foaming agent, a foaming assistant, an abrasive, a humectant, a sweetener, a preservative, an enzyme, a pH regulator, a bactericide, a medicinal component, a pigment, a colorant and flavoring agent.

The orally-acceptable dentifrice vehicle used to prepare an embodiment of the present invention comprises a water-phase, containing a humectant therein. Examples of the possible humectants included in the present invention include glycerin, sorbitol, propylene glycol, polyethylene glycol, xylitol, maltitol, lactitol and trehalose.

The humectant can include glycerin, sorbitol, xylitol, and/or propylene glycol of molecular weight in the range of 200-1,000; but, other humectants and mixtures thereof may also be employed. The humectant concentration typically totals about 5 to about 70% by weight of the oral composition. In an embodiment of the present invention, the humectant comprises about 30% to about 50% by weight of the composition. Water is a preferred diluent and in some compositions, such as mouthwashes and whitening liquids, it is commonly accompanied by an alcohol, e.g., ethanol. The weight ratio of water to alcohol in a mouthwash composition is generally about 1:1 to about 20:1, for example about 3:1 to about 20:1 or about 4:1 to about 10:1.

Reference hereto to sorbitol refers to the material typically commercially available as a 70% aqueous solution. Water is present typically in amount of at least about 10% by weight, and generally about 25 to 70% by weight of the oral composition. Water employed in the preparation of commercially suitable toothpastes should preferably be deionized and free of organic impurities, such as USP grade water. These amounts of water include the free water which is added plus that which is introduced with other materials such as with sorbitol.

Xylitol is a non-cariogenic carbohydrate and has a variety of uses including, but not limited to, a non-cariogenic sweetener, a humectant, and an anti-caries agent. Reference here to xylitol refers to the material typically commercially available and is typically present in a concentration range of about 0.1 to about 5% by weight.

It is contemplated that diamond particles or diamond dust present included in the dentifrice or polishing composition of the present invention is considered to be an abrasive component of the invention. In an embodiment, the diamond particles are present in a size range of about 0.01 µm to about 5.0 µm in diameter. In another embodiment, the diamond particles are present in a size range of about 0.05 µm to about 1.0 µm in diameter. In yet another embodiment, the diamond particles are present in a size range of about 0.02 µm to about 0.8 µm. In another embodiment, the diamond particles are present in a size range of about 0.05 µm to 0.6 µm. In a further embodiment, the diamond particles are present in a size range of about 0.1 µm to about 0.5 µm.

The diamond particulates included in the present composition can be from any commercially available source. It is typically sold in various sizes or meshes and is used primarily in the grinding and polishing arts. It is contemplated that the diamond powder included in the present composition is of superabrasive quality. The diamond particles are also available in mesh sizes. In an embodiment, the diamond particles are present in a size range of about 8000 to about 60,000 mesh. In another embodiment, the diamond particles are present in a size range of about 14,000 to about 60,000 mesh. In yet another embodiment, the diamond particles are present in a size range of about 28,000 to about 60,000 mesh.

The diamond particles can be obtained from any commercially available source. In an embodiment, the diamond particles obtained were in a size range of about 0.01 to about 0.5 µm in diameter (Diamond Technologies, Ltd., Bangkok, 10500, Thailand).

The concentration of the diamond powder in the composition of the present invention also contributes to its effectiveness as a cleaning and polishing agent. It is understood that the diamond particulates included in the present invention contribute to the higher gloss values obtained when compared to standard dentifrices or polishes. The concentration of the components and of the diamond powder included in the present invention is expressed in percent by weight. In an embodiment, the diamond particles included in the present invention can comprise between about 0.001% to about 1.0% of the total composition by weight. In another embodiment, the diamond particles of the present invention can comprise between about 0.005% to about 0.5% of the total composition by weight. In a further embodiment, the diamond particles of the present invention can comprise between about 0.005% to about 0.05% of the total composition by weight. In yet another embodiment, the diamond particles of the present invention can comprise between about 0.002% to about 0.02% of the total composition by weight. In another embodiment, the diamond particles of the present invention can comprise between about 0.01% to about 0.02% of the total composition by weight.

While it is contemplated that the diamond particulates comprise the abrasive component of the present invention, however, other typical dental abrasives can also be included in conjunction with the diamond particulates. In an embodiment of the present invention other abrasive agents included in the present invention comprise silica abrasives such as precipitated silica, silica gel, aluminosilicate and zirconosilicate, secondary calcium phosphate dihydrate or anhydrate, calcium pyrophosphate, calcium carbonate, alumina, aluminum hydroxide, magnesium acetate, tertiary magnesium phosphate, zeolite and synthetic resin abrasives. In an embodiment, commercially available silicas can be used. For example, silicas such as SIDENT® 9 and SIDENT® 22 made by Degussa are used (Degussa Corp. Parsippany, N.J.). These silicas have low oil absorption and medium hardness, and have a particle size of between about 9 and about 22 microns in diameter. However, a range of between about 2 and about 30 microns in diameter can be used in the present invention.

Commercially available abrasives may be used in combination with the diamond powder and include precipitated silicas having a mean particle size of up to about 20 microns, such as ZEODENT® 115 (J. M. Huber Chemicals Division, Havre de Grace, Md.), or SYLODENT® 783 (Davison Chemical Division of W.R. Grace & Co. Columbia, Md.). Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more additional abrasives are optionally present in an abrasive effective total amount, typically about 5% to about 70%, for example about 10% to about 50% or about 15% to about 30% by weight of the composition. Average particle size of an abrasive, if present, is generally about 0.1 to about 30 μm, for example about 1 to about 20 μm or about 5 to about 15 μm.

Sweetening agents of the present invention include sodium saccharin, aspartame, sucralose, thaumatin, acesulfame potassium, stevioside, stevia extract, paramethoxy cinnamic aldehyde, neohesperidyl dihydrochalcone and perillartine. Sweeteners among those useful herein also include orally acceptable natural or artificial, nutritive or non-nutritive sweeteners. Such sweeteners in the present invention can include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5% by weight, optionally from about 0.01% to about 1% by weight.

Plant extracts among those useful herein include pine, licorice, cassia seed, cinnamon, nothosmyrnium root, sophora, lonicera flower, platycodon, green tea, dayflower, Korean angelica root, liriope rhizome, moutan, Arabian myrrh, seseleos radix, Angelicae Dahuricae Radix, Lagerstroemia indica, morus bark, ginger, sanguinaria, asarum, cimicifuga, Chinese galls, grapefruit seed, lycium root, cnidium, Alpinia katsumadai Hayata, gardenia, Lythrum salicaria L., dandelion, propolis, flavonoid, nepta herb, Reynoutria japonica Houtt., scutellaria, machilia, black adzuki bean, camomile, ratanhia or sage oil. In an embodiment, the plant extract is a combination of two or more plant extracts. In another embodiment, the plant extract is a combination of three or more different plant extracts, for example, camomile flower extract, sage leaf extract and peppermint leaf extract. Plant extracts can be obtained from any commercially available source. In one embodiment, extracts were obtained from Alban Muller International, Vincennes, France. Plant extracts are provided in an embodiment in a concentration between about 0.1% to about 5% by weight.

In an embodiment, a combination of three plant extracts is contemplated. The combination includes camomile flower extract, sage leaf extract and peppermint leaf extract. The three plant extract is provided in an embodiment in a concentration between about 0.1% to about 5% by weight.

Plant extracts contemplated herein also include aloe vera extracts, such as aloe vera oil. U.S. Pat. No. 3,892,853 to Henry H. Cobble teaches the use of aloe vera gel by physicians and dentists in relieving pain and in promoting healing of topical and other lesions. Other toothpastes use aloe vera, a bacteriostatic or bactericidal agent, to remove bacteria which are known to cause plaque. This has also been noted to have a natural antibiotic action, see for example, U.S. Pat. No. 5,294,434 to King et al. In an embodiment, the composition of the present invention comprises aloe vera oil in gel form; however other forms of aloe vera can be used.

Flavoring agents among those useful herein include any material or mixture of materials operable to enhance the taste of the present composition. Any orally acceptable natural or synthetic flavorant can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methyl salicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include methol, menthyl acetate, menthyl lactate, camphor, eucalyptus oil, eucalyptol, anethole, eugenol, cassia, oxanone, .alpha.-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), 1-menthol, carvone, anethole, eugenol, limonene, peppermint oil, spearmint oil, ocimene, n-amyl alcohol, citronellol, a-terpineol, methyl salicylate, methyl acetate, citronellol acetate, cineol, linalool, ethyl linalool, capsaicin and mixtures thereof. One or more flavorants are optionally present in a total amount of about 0.01% to about 5% by weight, optionally in various embodiments from about 0.05 to about 2% by weight, from about 0.1% to about 2.5% by weight, and from about 0.1 to about 0.5% by weight.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20% by weight, for example about 0.01% to about 10% by weight or about 0.1% to about 5% by weight.

Fragrances and aromas may also be added to the dentifrice composition. For example, aromas of peppermint or spearmint are commercially available. In an embodiment, a fragrance is added to the dentifrice composition in a concentration of about 0.01% to about 5% by weight. In another embodiment, a fragrance is added to the dentifrice in a concentration of about 0.5 to about 1.5% by weight. Aromas and fragrances can be obtained from any commercially available source. In one embodiment, extracts were obtained from Curt Georgi GmbH & Co. KG, 71034 Boeblingen, Germany.

The dentifrice composition of the present invention may include other various effective ingredients include water-soluble phosphoric acid compounds such as potassium salt or sodium salt of orthophosphoric acid, allantoin chlorohydroxyaluminum, hinokitiol, lysozyme chloride, sodium chloride, epsilon-aminocaproic acid, dl-tocopherol acetate, azulene, copper compounds such as sodium copper chlorophyllin and copper gluconate, aluminum lactate, strontium chloride, potassium nitrate, berberine, hydroxamic acid and derivatives thereof, sodium tripolyphosphate, zeolite, dextranase, mutanase, amylase, methoxyethylene, maleic anhydride copolymer, polyvinylpyrrolidone, epidihydrocholesterin, dihydrocholesterol, zinc citrate, clove, rosemary, scutellaria roots, safflower, and the like, .alpha.-bisabolol, chlorhexidine salts, triclosan, cetylpyridinium chloride, benzethonium chloride, and trichlorocarbanilide.

It is understood that for pH modifying agents among those useful herein include acidifying agents to lower pH, basifying agents to raise pH, and buffering agents to control pH within a desired range. For example, one or more compounds selected from acidifying, basifying, and buffering agents can be included to provide a pH of about 2 to about 10, or in various embodiments from about 2 to about 8, from about 3 to about 9, from about 4 to about 8, from about 5 to about 7, from about 6 to about 10, and from about 7 to about 9. Any orally acceptable pH modifying agent can be used including, but not limited to, those described above herein. One or more pH modifying agents are optionally present in a total amount effective to maintain the composition in an orally acceptable pH range.

The compositions of the present invention optionally comprise one or more additional active ingredient(s), which is operable for the prevention or treatment of a condition or disorder of hard or soft tissue of the oral cavity, the prevention or treatment of a physiological disorder or condition, or to provide a cosmetic benefit. In various embodiments, the active ingredient is a "systemic active ingredient" which is operable to treat or prevent a disorder which, in whole or in part, is not a disorder of the oral cavity. In various embodiments, the active is an "oral care active ingredient" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, periodontal actives, abrasives, breath freshening agents, malodour control agents, tooth desensitizers, salivary stimulants, antibacterial agents, and combinations thereof. It is understood that while general attributes of each of the above categories of actives may differ, there may some common attributes and any given material may serve multiple purposes within two or more of such categories of actives.

The compositions of the present invention optionally comprise an antimicrobial (e.g., antibacterial) agent. One or more such agents can be present. Suitable examples include without limitation copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like. Other suitable antibacterial agents include non-ionic and anionic antibacterial agents known to one of skill in the art. For example, non-ionic antibacterial agents include the substantially water insoluble, noncationic antibacterial agents such as alkylphenoxy phenols; cycloalkyl-phenoxyphenols; 9,10-dihydrophenanthrenol; alkylphenols; cycloalkyl-phenols; phenolic compounds; halogenated carbanilides; halogenated salicylanilides; benzoic esters; halogenated diphenyl ethers, and mixtures thereof. A particularly suitable non-ionic antibacterial agent is a diphenyl ether such as 2,4,4'-trichloro-2'-hydroxydiphenyl ether (Triclosan) and 2,2'-dihydroxy-5,5'-dibromodiphenyl ether. A further illustrative list of useful antibacterial agents is provided in U.S. Pat. No. 5,776,435 to Gaffar et al. One or more antimicrobial agents are optionally present in an antimicrobially effective total amount, typically about 0.05% to about 10%, for example about 0.1% to about 3% by weight, of the composition.

The compositions of the present invention optionally comprise an antiplaque (e.g., plaque disrupting) agent. One or more such agents can be present in an antiplaque effective total amount. Suitable antiplaque agents include without limitation xylitol, stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

The compositions of the present invention optionally comprise a desensitizing, or tooth sensitivity protecting agent. One or more such agents can be included. Suitable desensitizing agents include, without limitation, potassium salts such as potassium citrate, potassium tartrate, potassium chloride, potassium sulfate and potassium nitrate. Another suitable desensitizing agent is sodium nitrate. Alternatively, or in addition, a local or systemic analgesic such as aspirin, codeine, acetaminophen, sodium salicylate or triethanolamine salicylate can be used. One or more desensitizing agents and/or analgesics are optionally present in a desensitizing and/or analgesic effective amount, typically about 0.05% to about 5%, for example about 0.1% to about 3% by weight, of the composition.

The ingredients of the present invention must be non-toxic, for example, the ingredients can meet or exceed food, cosmetic or U.S.P. grade materials, or otherwise are suitable for use in an oral care product. The gelling agents include an edible gum and a seaweed extract, both of which are food or cometic quality and have been used in a variety of food applications. All of the above ingredients are readily available in U.S.P. or food grade.

It is contemplated that an effective amount of recommended and well-known preservatives are included in the composition of the present invention, such as methyl paraben and propyl paraben. These preservatives are soluble in glycerin and other equivalent humectants. Methyl and propyl paraben may be added in the present invention in typical effective amounts of about 0.2 and about 0.1 weight percent respectively.

In various embodiments, toothpastes, creams and gels contain a natural or synthetic thickener or gelling agent, which, other than silica thickeners, include natural and synthetic gums and colloids. In a still further embodiment a composition of the invention comprises at least one thickening agent, useful for example to impart a desired consistency and/or mouth feel to the composition. Any orally acceptable thickening agent can be used, including without limitation carbomers, also known as carboxyvinyl polymers, carrageenans, also known as Irish moss and more particularly i-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica, cocaimidopropyl betaine and the like. One or more thickening agents are optionally present in a total amount of about 0.01% to about 15%, for example about 0.1% to about 10% or about 0.2% to about 5% by weight of the composition.

The gums that are contemplated for use as thickeners in the present invention also include gum tragacanth, a relatively well-known water soluble, edible gum and such gums have been used in prior dental paste and cream formulations. Agar is a commonly known edible, seaweed extract. It is considered to be a non-sulfated linear molecule composed of alternating residues of 1,3, beta D-galactopyranose and 1,4-3,6 anhydro-alpha-L-galoctopyranose together with a non-gelling or very weak gelling agaropectin composed of a complicated acidic polymer containing ester sulfate groups and organic acid groups. Other seaweed extracts in the form of commercially prepared propylene glycol alginate, algins or certain carrageenans can be substituted for agar.

Foam modulators useful herein include materials operable to increase amount, thickness, or stability of foam generated by the composition (e.g., dentifrice or polish compositions) upon agitation. Any orally acceptable foam modulator can be used, including polyethylene glycols (PEGs), also known as polyoxyethylenes. High molecular weight PEGs are suitable, including those having an average molecular weight of about 200,000 to about 7,000,000, for example about 500,000 to about 5,000,000 or about 1,000,000 to about 2,500,000. one or more PEGs are optionally present in a total amount of about 0.1% to about 10% by weight, for example about 0.2% to about 5% by weight or about 0.25% to about 2% by weight.

Methods are provided to polish or whiten dental surfaces and/or treat or prevent dental caries in a human or animal subject comprising administering a safe and effective amount of a dentifrice or polish composition to the dental surfaces of the subject, using a brush or other suitable applicator or appliance, the composition comprising: water, a humectant and diamond powder wherein the diamond powder is present in a range of about 0.001 to about 0.1% by weight. As used herein "animal subject" includes higher order non-human mammals such as canines and felines. The dentifrice or polish composition is contacted with dental, porcelain or composite covered surfaces of the mammalian subject to thereby provide cleaning and polishing of said surfaces of the teeth in a highly efficacious manner.

In an embodiment, the dentifrice composition contains aloe vera extract in various forms, including powder, oil or gel form. The aloe vera extract can be from any commercially available source that is food grade or USP grade, or otherwise suitable for an oral care product. For example, the aloe vera oil can be obtained from Textron Technica S. L. (Barcelona, Spain 08402), or from Florida Food Products, Inc. (Eustis, Fla.). It is contemplated that the aloe vera extract can be present in the dentifrice composition in a concentration of about 0.01% to about 1% by weight of the composition.

In various embodiments, it is preferred that the dentifrice or polish composition of the present invention is applied and contacted with the dental enamel or porcelain or composite surfaces of the teeth or implant or other restoration. In an embodiment, the dentifrice or polish prepared in accordance with the present invention is preferably applied regularly to dental enamel, or porcelain, or composite surfaces, including crowns or other implantable oral devices, such as on a daily basis, at least one time daily for multiple days, but alternately every second or third day. In another embodiment, the dentifrice composition is applied to the dental or porcelain surfaces from 1 to 3 times daily, for at least 2 weeks up to 8 weeks, from two years to three years, or more up to lifetime.

The dentifrice or polish composition of the present invention is applied and contacted to the surfaces of the teeth dental enamel, porcelain or composite surfaces, including crowns or other implantable oral devices by any known means, including, but not limited to, toothbrushes, applicators, swabs, dental instruments including motorized or powered implements as well as manual implements.

The dentifrice compositions of the present invention may be prepared by suitably mixing the ingredients. For instance, in the preparation of a dentifrice, the abrasives, including the diamond powder, are dispersed in a mixture of dry ingredients, e.g., humectants, surfactants, flavoring, additional thickener are then added and mixed. The ingredients are then mixed with deionized water for about 15-30 minutes. The resulting product is then packaged.

While it is contemplated that application of the dentifrice of the present invention will be on dental surfaces of natural teeth as well as porcelain, ceramic and composite dental surfaces, it is also an embodiment of the invention to apply the composition on dental implants and also to older dental restorative devices, such as bridgework, that have been used by a patient for years. In one embodiment, the dentifrice of the present invention can be used to restore discolored veneers or crowns or bridgework to a significantly whiter color, and glossier and smoother finish.

It is contemplated that the dentifrice or polish composition can be included in a kit. In an embodiment, the kit of the present invention comprises the dentifrice or polish composition and a brush or other suitable applicator or appliance. In another embodiment, the kit of the present invention may comprises the dentifrice or polish composition and a brush or other suitable applicator or appliance, along with instructions in printed form.

EXAMPLES

A dentifrice composition is prepared according to the following table. In an embodiment, the composition of the tooth polish of the present invention includes the following:

| Ingredient | Percent by weight (wt %) |
| --- | --- |
| Water (demi) | 10-70 |
| Xanthan gum | 0.1-10 |
| Sorbitol | 5.0-30 |
| Glycerin | 5.0-30 |
| Plant extract (chamomile flower extract, sage leaf extract, peppermint leaf extract) | 0.1-5.0 |
| Xylitol | 0.05-5.0 |
| Sodium monofluorophosphate (USP) | 0.1-2.0 |
| Silica-SIDENT 9 (Degussa) | 0.1-20.0 |
| Silica-SIDENT 22 S (Degussa) | 0.1-20.0 |
| TiO$_2$ (Titanium Dioxide) | 0.1-5.0 |
| Diamond Powder MSY 0.5µ | 0.001-1.0 |

Example 1

A dentifrice composition is prepared according to the following table. In an embodiment, the composition of the tooth polish of the present invention includes the following:

| Ingredient | Percent by weight (wt %) |
| --- | --- |
| Water (demi) | 23.49 |
| Xanthan gum | 1.00 |
| Sorbitol | 20.00 |
| Glycerin | 21.00 |
| Plant extract (chamomile flower extract, sage leaf extract, peppermint leaf extract) | 0.50 |
| Xylitol | 0.20 |
| Sodium monofluorophosphate (USP) | 0.70 |
| Silica-SIDENT 9 (Degussa) | 6.00 |
| Silica-SIDENT 22 S (Degussa) | 13.00 |
| TiO$_2$ (Titanium Dioxide) | 1.00 |
| Diamond Powder MSY 0.5μ | 0.01 |
| Cocamidopropyl Betaine | 2.00 |
| *Aloe vera* oil gel | 0.10 |
| Mint Fragrance | 1.00 |

Example 2

In another embodiment for whitening, the composition of the tooth polish of the present invention includes the following:

| Ingredient | Percent by weight (wt %) |
| --- | --- |
| Water (demi) | 23.49 |
| Xanthan gum | 1.00 |
| Sorbitol | 20.00 |
| Glycerin | 21.00 |
| Plant extract (chamomile flower extract, sage leaf extract, peppermint leaf extract) | 0.50 |
| Xylitol | 0.20 |
| Sodium monofluorophosphate (USP) | 0.70 |
| Silica-SIDENT 9 (Degussa) | 6.00 |
| Silica-SIDENT 22 S (Degussa) | 13.00 |
| TiO$_2$ (Titanium Dioxide) | 1.00 |
| Diamond Powder MSY 0.5μ | 0.01 |
| Cocamidopropyl Betaine | 2.00 |
| *Aloe vera* oil gel | 0.10 |
| Mint Fragrance | 1.00 |
| Sodium Bicarbonate (NaHCO$_3$) | 5.00 |

Example 3

In an embodiment useful for patients with sensitive teeth, the composition of the tooth polish of the present invention includes the following:

| Ingredient | Percent by weight (wt %) |
| --- | --- |
| Water (demi) | 23.49 |
| Xanthan gum | 1.00 |
| Sorbitol | 20.00 |
| Glycerin | 21.00 |
| Plant extract (chamomile flower extract, sage leaf extract, peppermint leaf extract) | 0.50 |
| Xylitol | 0.20 |
| Sodium monofluorophosphate (USP) | 0.70 |
| Silica-SIDENT 9 (Degussa) | 6.00 |
| Silica-SIDENT 22 S (Degussa) | 13.00 |
| TiO$_2$ (Titanium Dioxide) | 1.00 |
| Diamond Powder MSY 0.5μ | 0.01 |
| Cocamidopropyl Betaine | 2.00 |
| *Aloe vera* oil gel | 0.10 |
| Mint Fragrance | 1.00 |
| Potassium Nitrate | 5.00 |

Example 4

In an embodiment, a plaque fighting composition of the tooth polish of the present invention includes the following:

| Ingredient | Percent by weight (wt %) |
| --- | --- |
| Water (demi) | 23.49 |
| Xanthan gum | 1.00 |
| Sorbitol | 20.00 |
| Glycerin | 21.00 |
| Plant extract (chamomile flower extract, sage leaf extract, peppermint leaf extract) | 0.50 |
| Xylitol | 0.50 |
| Sodium monofluorophosphate (USP) | 0.70 |
| Silica-SIDENT 9 (Degussa) | 6.00 |
| Silica-SIDENT 22 S (Degussa) | 13.00 |
| TiO$_2$ (Titanium Dioxide) | 1.00 |
| Diamond Powder MSY 0.5μ | 0.01 |
| Cocamidopropyl Betaine | 2.00 |
| *Aloe vera* oil gel | 0.10 |
| Mint Fragrance | 1.00 |

Example 5

In an embodiment, a tartar control composition of the tooth polish of the present invention includes the following:

| Ingredient | Percent by weight (wt %) |
| --- | --- |
| Water (demi) | 23.49 |
| Xanthan gum | 1.00 |
| Sorbitol | 20.00 |
| Glycerin | 21.00 |
| Plant extract (chamomile flower extract, sage leaf extract, peppermint leaf extract) | 0.50 |
| Xylitol | 0.20 |
| Sodium monofluorophosphate (USP) | 0.70 |
| Silica-SIDENT 9 (Degussa) | 6.00 |
| Silica-SIDENT 22 S (Degussa) | 13.00 |
| TiO$_2$ (Titanium Dioxide) | 1.00 |
| Diamond Powder MSY 0.5μ | 0.01 |
| Cocamidopropyl Betaine | 2.00 |
| *Aloe vera* oil gel | 0.10 |
| Mint Fragrance | 1.00 |
| Zinc Citrate | 5.00 |

Example 6

In an embodiment, an extra strength composition of the tooth polish of the present invention includes the following:

| Ingredient | Percent by weight (wt %) |
| --- | --- |
| Water (demi) | 23.49 |
| Xanthan gum | 1.00 |
| Sorbitol | 20.00 |
| Glycerin | 21.00 |
| Plant extract (chamomile flower extract, sage leaf extract, peppermint leaf extract) | 0.50 |
| Xylitol | 0.20 |
| Sodium monofluorophosphate (USP) | 0.70 |
| Silica-SIDENT 9 (Degussa) | 6.00 |
| Silica-SIDENT 22 S (Degussa) | 13.00 |
| TiO$_2$ (Titanium Dioxide) | 1.00 |
| Diamond Powder MSY 0.5μ | 0.05 |
| Cocamidopropyl Betaine | 2.00 |
| *Aloe vera* oil gel | 0.20 |
| Mint Fragrance | 1.00 |
| Zinc Citrate | 5.00 |

Example 7

In an embodiment, a milder polish composition of the tooth polish of the present invention includes the following:

| Ingredient | Percent by weight (wt %) |
|---|---|
| Water (demi) | 23.49 |
| Xanthan gum | 1.00 |
| Sorbitol | 20.00 |
| Glycerin | 21.00 |
| Plant extract (chamomile flower extract, sage leaf extract, peppermint leaf extract) | 0.50 |
| Xylitol | 0.20 |
| Sodium monofluorophosphate (USP) | 0.70 |
| Silica-SIDENT 9 (Degussa) | 6.00 |
| Silica-SIDENT 22 S (Degussa) | 13.00 |
| TiO$_2$ (Titanium Dioxide) | 1.00 |
| Diamond Powder MSY 0.5µ | 0.005 |
| Cocamidopropyl Betaine | 2.00 |
| Aloe vera oil gel | 0.10 |
| Mint Fragrance | 1.00 |
| Zinc Citrate | 5.00 |

Example 8

A controlled study was performed by the College of Dental Medicine at Nova Southeastern University in Ft. Lauderdale Fla. The study was designed to determine how well the inventive dentifrice composition polished surfaces using a standard brushing protocol on eight different porcelain, ceramic and composite surfaces against a standard toothpaste (Regular CREST® toothpaste) and a standard polish (SUPERSMILE® a mixture of bicarbonate of soda and other components). Gloss and Roughness of the samples were measured at the start (baseline) and after one year of simulated brushing. The brushing was performed on a V-8 Cross Brushing Machine (Sabri Dental Enterprises, Inc., Ill.). The samples were brushed for 10,000 cycles which is equivalent to one year of brushing. The brushes used were standard American Dental Association manual toothbrushes (Henry Schein, Inc. Melville, N.Y.). A standard slurry was made using 37 g of polish and 37 ml of distilled water to polish the test surfaces. Only one surface was brushed in each test.

Gloss Results. Gloss of the brushed surface was measured using a Novo-Curve curved surface glossmeter (Rhopoint Instrumentation, Ltd. 12 Beeching Road, Bexhill-on-Sea, East Sussex, TN39 3LG, UK).

Testing showed that the highest gloss scores during brushing were found with dentifrice or polish of the present invention and the standard polish. However, gloss scores taken after brushing was completed found that dentifrice or polish of the present invention produced the highest gloss score, while the standard polish actually had the lowest after brushing score.

Roughness Results. Roughness of the test surfaces was measured using a MicroXam optical surface profiler (Phase-Shift, Inc. Tucson Ariz.). The testing showed that, overall, the standard control test toothpaste had the highest scores for roughness. The dentifrice or polish of the present invention had only slightly greater roughness scores than the standard polish, thus it produced a smoother tooth surface than the standard toothpaste.

The results from both tests show that dentifrice or polish of the present invention comprising diamond particles produced a glossier and a smoother surface than standard toothpaste, and was safe to use on teeth on a daily basis.

Example 9

The dentifrice or polish composition according to Example 1 is administered to a human subject having existing porcelain veneers or composite on their teeth. The composition is applied with a toothbrush to the dental surfaces twice daily for three months to whiten and polish the teeth and veneer surfaces and reduce plaque formation. After application, the natural tooth, porcelain and composite surfaces have increased gloss and whiteness and a smoother finish.

Example 10

The dentifrice or polish composition according to Example 1 is applied to older dental restorations that have become discolored after years of use. The composition is applied with a toothbrush twice daily for two weeks to three months to whiten and polish the teeth and veneer surfaces and reduce plaque formation. After application, the whiteness, gloss and luster of the older restorations are improved significantly.

Example 11

A controlled study is designed to determine how well the inventive dentifrice composition polished surfaces using a standard brushing protocol on eight different porcelain, ceramic and composite surfaces that are made to simulate older aged dental surfaces and restorations against a standard toothpaste (Regular CREST® toothpaste) and a standard polish (SUPERSMILE® a mixture of bicarbonate of soda and other components). The aging will be simulated by pre-abrading the various surfaces sufficiently to mimic two or more years of use in a patient. Gloss and Roughness of the samples will be measured at the start (baseline) and after one year of simulated brushing. The brushing will be performed on a V-8 Cross Brushing Machine (Sabri Dental Enterprises, Inc., Ill.). The samples will be brushed for 10,000 cycles which is equivalent to one year of brushing. The brushes used will be standard American Dental Association manual toothbrushes (Henry Schein, Inc. Melville, N.Y.). A standard slurry will be made using 37 g of polish and 37 ml of distilled water to polish the test surfaces. Only one surface will be brushed in each test.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A dentifrice or polish composition consisting essentially of:
   (a) an orally acceptable vehicle;
   (b) diamond particles disposed within the orally acceptable vehicle;
   (c) a humectant and a binder disposed within the vehicle; and,
   (d) sodium fluoride and xylitol also disposed within the vehicle;
   wherein the composition is effective for whitening teeth having porcelain surfaces and suitable for application to teeth in the oral cavity;
   wherein the diamond particles constitute about 0.01 to about 0.02 percent by weight of the composition, and have a size range of about 0.03 μm to about 0.07 μm in diameter.

2. The dentifrice or polish of claim 1, wherein the humectant is selected from the group consisting of: glycerin, sorbitol, propylene glycol, polyethylene glycol, xylitol, maltitol, lactitol and trehalose, in a concentration of about 30% to 70% by weight of the composition.

3. The dentifrice or polish composition of claim 1, wherein the binder is selected from the group consisting of: xanthan gum and other gums, sodium alginate, sodium carboxymethylcellulose, carrageenan, xanthan gum, sodium polyacrylate, hydroxyethyl cellulose, hydroxypropyl cellulose, pectin, tragacanth gum, arabic gum, guar gum, karaya gum, locust bean gum, gellan gum, tamarind gum, Psyllium seed gum, polyvinyl alcohol, sodium chondroitin sulfate, and methoxyethylene-maleic anhydride copolymer.

4. The dentifrice or polish composition of claim 1, wherein said composition further comprises an abrasive agent.

5. The dentifrice or polish of claim 4, wherein the abrasive agent is selected from the group consisting of: precipitated silica, silica gel, aluminosilicate and zirconosilicate, secondary calcium phosphate dihydrate or anhydrate, calcium pyrophosphate, calcium carbonate, alumina, aluminum hydroxide, magnesium acetate, tertiary magnesium phosphate, zeolite and synthetic resin abrasives.

6. The dentifrice or polish composition of claim 1, further comprising one or more of a flavoring agent, a colorant, an anti-caries agent, a pH modifying agent, plant extracts, antimicrobial agents, anti-plaque agents, thickeners, gums and foam modulators.

7. A dentifrice or polish composition effective for whitening teeth having porcelain surfaces suitable for application to teeth in the oral cavity having the following composition:
   diamond particles having a size range of about 0.1 μm to about 0.5 μm and comprising between about 0.002% to about 0.05% of the total composition by weight disposed within an orally acceptable vehicle;
   both a humectant in a concentration of about 5 to about 70% by weight of the composition and also a binder disposed within the vehicle;
   sodium fluoride also disposed within the vehicle, the binder having a concentration of about 0.1% to about 10% by weight of the composition;
   a plant extract in a concentration of about 0.1% to about 5% by weight of the composition also disposed within the vehicle; and,
   an abrasive agent in a concentration of about 15% to about 30% by weight of the composition disposed within the vehicle.

8. The dentifrice or polish composition of claim 7, further comprising one or more of a flavoring agent, a colorant, an anti-caries agent, a pH modifying agent, antimicrobial agents, anti-plaque agents, thickeners, gums and foam modulators.

9. A dentifrice or polish effective for whitening teeth having porcelain surfaces suitable for application to teeth in the oral cavity having the following composition: TABLE-US-00009 Ingredient Percent by weight (wt %) Xanthan gum 1.00 Sorbitol 20.00 Glycerin 21.00 Plant extract (chamomile flower extract, sage 0.50 leaf extract, peppermint leaf extract) Xylitol 0.20 Sodium monofluorophosphate (USP) 0.70 Silica-Sident 9 (Degussa) 6.00 Silica-Sident 22 S (Degussa) 13.00 TiO.sub.2 (Titanium Dioxide) 1.00 Diamond Powder MSY 0.5.mu. 0.01 Cocamidopropyl Betaine 2.00 Aloe vera oil gel 0.10 Aroma Powermint 1.00 and said composition including the remainder as water up to 100% by weight.

10. The dentifrice or polish composition of claim 9, wherein said composition further comprises a whitening agent.

11. The dentifrice or polish composition of claim 10, wherein said whitening agent comprises about 5% by weight of Na.sub.2HCO.sub.3.

12. The dentifrice or polish composition of claim 9, wherein said composition further comprising a desensitizing agent.

13. The dentifrice or polish composition of claim 12, wherein said desensitizing agent comprises about 5% by weight of potassium nitrite.

14. The dentifrice or polish composition of claim 9, wherein said composition further comprises a tartar control agent.

15. The dentifrice or polish composition of claim 14, wherein said tartar control agent comprises about 0.5% by weight of zinc citrate.

16. The dentifrice or polish composition of claim 9, wherein said composition further comprises an antiplaque agent.

17. The dentifrice or polish composition of claim 16, wherein said tartar control agent comprises about 0.5% by weight of xylitol.

18. A method of cleaning or polishing a dental surface, wherein said method comprises the steps of applying the dentifrice or polish of claim 1 to a dental surface, and brushing said dental surface with said composition for a therapeutically effective period of time.

19. A method of cleaning or polishing an older dental surface, wherein said method comprises the steps of applying the dentifrice or polish of claim 1 to a dental surface, and brushing said dental surface with said composition for a therapeutically effective period of time.

20. The dentifrice or polish composition of claim 7, wherein said composition further comprises 0.5 to 5.0% by weight of xylitol.

21. The dentifrice or polish composition of claim 7, wherein said composition further comprises about 0.1 to 2.0% by weight of sodium monofluorophosphate or sodium fluoride (USP).

22. The dentifrice or polish composition of claim 7, wherein said composition further comprises about 0.5 to 5.0% by weight of xylitol and about 0.1 to 2.0% by weight of sodium monofluorophosphate or sodium fluoride (USP).

* * * * *

UNITED STATES PATENT AND TRADEMARK OFFICE
CERTIFICATE OF CORRECTION

PATENT NO. : 9,724,541 B2  
APPLICATION NO. : 12/418927  
DATED : August 8, 2017  
INVENTOR(S) : Kao et al.

Page 1 of 1

It is certified that error appears in the above-identified patent and that said Letters Patent is hereby corrected as shown below:

On the Title Page

Item (75) should read:  
(75) Inventors: Lisa Marie Kao, Miami Beach, FL (US);  
Garcia Godoy, Cordova, TN (US)

Signed and Sealed this  
Twenty-seventh Day of February, 2018

Andrei Iancu  
*Director of the United States Patent and Trademark Office*